United States Patent
Xu et al.

(10) Patent No.: US 9,057,596 B2
(45) Date of Patent: Jun. 16, 2015

(54) DEVICE AND METHOD FOR MONITORING ROTOR BLADES OF A TURBINE

(75) Inventors: Qin Xu, Bôle (CH); Jonathan Geisheimer, Neyruz (CH); Gérald Egger, Villars-sur-Glâne (CH); Maddalena Violetti, Lausanne (CH); Anja Skrivervik Favre, Champvent (CH)

(73) Assignee: MEGGITT SA (CH)

( * ) Notice: Subject to any disclaimer, the term of this patent is extended or adjusted under 35 U.S.C. 154(b) by 339 days.

(21) Appl. No.: 13/609,863

(22) Filed: Sep. 11, 2012

(65) Prior Publication Data

US 2013/0068024 A1 Mar. 21, 2013

(30) Foreign Application Priority Data

Sep. 16, 2011 (EP) .................... 11181622

(51) Int. Cl.
 *G01N 29/14* (2006.01)
 *G01B 7/14* (2006.01)
 *G01B 15/00* (2006.01)

(52) U.S. Cl.
 CPC ......... *G01B 7/14* (2013.01); *G01N 29/14* (2013.01); *G01B 15/00* (2013.01)

(58) Field of Classification Search
 USPC .............. 73/660, 655, 593, 618–620, 587; 702/183–188; 324/644
 See application file for complete search history.

(56) References Cited

U.S. PATENT DOCUMENTS

| | | | | |
|---|---|---|---|---|
| 6,823,736 B1 * | 11/2004 | Brock et al. | ..... | 73/587 |
| 7,095,221 B2 * | 8/2006 | Bosselmann et al. | ..... | 324/71.1 |
| 7,215,252 B2 * | 5/2007 | Schenck | ..... | 340/686.1 |
| 7,373,823 B2 * | 5/2008 | Bosselmann et al. | ..... | 73/620 |
| 7,397,421 B2 * | 7/2008 | Smith | ..... | 342/192 |
| 2005/0280549 A1 * | 12/2005 | Schenck | ..... | 340/686.6 |
| 2006/0000283 A1 * | 1/2006 | Twerdochlib | ..... | 73/593 |
| 2009/0134884 A1 * | 5/2009 | Bosselmann et al. | ..... | 324/644 |
| 2010/0066387 A1 * | 3/2010 | Bosselmann et al. | ..... | 324/644 |

FOREIGN PATENT DOCUMENTS

EP 2042830 * 4/2009
WO WO 2010/112278 * 10/2010

* cited by examiner

*Primary Examiner* — Helen Kwok
(74) *Attorney, Agent, or Firm* — Ostrolenk Faber LLP

(57) ABSTRACT

A device and a method for monitoring the operational state of rotor blades of a turbine from a position facing the blade tip of a passing rotor blade: A wavesource generates an electromagnetic wave and a wave guide directs the wave towards the blade tip. The waveguide is included in a resonator defining at least one discrete resonance frequency of the wave on the waveguide. An aperture at its front end emits an energy fraction of the wave toward the blade tip. The frequency of the wave is adjusted to the resonance frequency of the resonator at the momentary operation conditions, and a measuring unit compares at least one measurement parameter of the wave directed towards the blade tip with the corresponding measurement parameter of the wave reflected from the blade tip.

21 Claims, 6 Drawing Sheets

DEVICE AND METHOD FOR MONITORING ROTOR BLADES OF A TURBINE

FIELD OF THE INVENTION

The invention relates to a device for monitoring the operational state of rotor blades of a turbine from a position facing the blade tip of a passing rotor blade, the device comprising a wavesource for generating an electromagnetic wave and a waveguide for directing the wave towards the blade tip. The invention further relates to a turbine comprising such a monitoring device and to a monitoring method of a generic kind.

BACKGROUND OF THE INVENTION

Driven by ever-increasing requirements for improved fuel efficiency, reduced undesirable emissions and reduced noise, future aero-engines and land-based turbines will have to incorporate new systems to monitor the turbine conditions, analyse the incoming data and modify operating parameters to optimise operations and thus achieve improved performance. Sensing technology is the foundation upon which such systems are based. New sensors that are able to operate under the harsh environment present in a turbine must be developed to enable the measurement of previously unmeasurable parameters critical for monitoring the overall health of the turbine. The potential benefits from those systems are significant and may be categorised into two primary areas: turbine efficiency and turbine maintenance. For both purposes, the monitoring of the operational state of the turbine's rotor blades is an essential requirement, in particular for a detailed understanding of the functioning and health of a turbine.

In order to perform an accurate measurement of the operational state of the rotor blades, a microwave sensor is typically mounted through a hole or attached to the inside of the engine case to enable the microwave sensor to cast its beam onto the blades, which will be rotating and subsequently passing by the sensor during engine operation. Yet the environment encountered in turbine engines is harsh with gas path temperatures exceeding 1300 K in high-pressure turbines and temperatures around 900 K in the rear stages of a high-pressure compressor of aero-engines, most often with a high thermal gradient as well. It is a dirty environment with oil, combustion by-products and other contaminants. A sensor being able to operate reliably at those extreme temperatures and in such a harsh environment is therefore a key component.

A sensor to solve this problem has been addressed in patent application No. US 2010/0066387 A1 which discloses a device for determining the distance between a rotor blade and a wall of a gas turbine surrounding the rotor blade. The device comprises a waveguide that guides electromagnetic waves with at least two frequencies. Waves with one of the frequencies are emitted from the sensor and reflected back by the rotor blade and waves with the other frequency are reflected by a sealing element at the end of the waveguide. The distance of the device with respect to the rotor blade is then determined by comparing phases of the waves.

A disadvantage of this sensor is that a temperature dependent expansion of the turbine walls, in which the device is mounted, also causes a corresponding expansion of the waveguide, making the desired distance determination inaccurate. The problem may be circumvented by subtracting the phase comparison values of the waves of the two frequencies from each other and assigning this value to a previously measured value for the distance under those temperature conditions, e.g. on the basis of a value table. Nevertheless, a more direct way of accounting for the temperature changes would be highly desirable in order to make sure that the momentary operating conditions of the turbine are met, which generally do not solely dependent on the temperature gradient. Apart from the reliability of the measurement, it would also be desirable to improve the detection performance, in particular to increase the measurement resolution, and to extend a monitoring of the rotor blades beyond the detection of the single parameter of a distance measurement in between the blade tips and the sensor.

OBJECTS AND SUMMARY OF THE INVENTION

Accordingly, it is an object of the present invention to avoid at least one of the above mentioned disadvantages and to provide an improved monitoring device and method, in which the harsh operation conditions within a turbine environment are accounted for.

Relating to the monitoring device, the invention suggests that the waveguide is included in a resonator defining at least one discrete resonance frequency of the wave on the waveguide and comprising an aperture at its front end through which an energy fraction of the wave can be emitted towards the blade tip. Thus, the resonator is provided in such a way that it supports at least one discrete resonance frequency of the wave on the waveguide. In this way, the resonator can be used to store inside electromagnetic energy of the wave at the resonance frequency. Due to the aperture at the front end, a fraction of the electromagnetic energy stored inside the resonator can be emanated from the resonator to interact with the rotor blades. Preferably, the back end of the resonator is short-circuited.

The resonance frequency of the wave can depend on the momentary operation conditions of the turbine and the resonator is preferably configured to support the resonance frequency shifting within a range of changing operation conditions. The device further comprises a frequency adjusting unit that is configured to set the frequency of the wave to the resonance frequency of the resonator at the momentary operation conditions. Thus, the monitoring device can be matched to momentary changes of operation conditions within the turbine environment by an adjustment of the wave frequency with respect to occurring changes of the resonance frequency of the resonator. Those operation conditions of the turbine environment affecting the resonance frequency of the resonator may comprise a temperature gradient of the propagation medium of the electromagnetic wave.

By further effectuating a comparison of at least one measurement parameter in between the outgoing and reflected wave, reliable informations about the operational state of a rotor blade can be deduced irrespective of the momentary operation conditions within the turbine environment. Accordingly, the device also comprises a measuring unit that is configured to compare at least one measurement parameter of the wave emitted towards the blade tip with the corresponding measurement parameter of the wave reflected from the blade tip. In this way, accurate measurements of the operational state of a rotor blade can be obtained even if the resonance frequency of the resonator shifts with temperature or due to other disturbing effects. Preferably, the measurement parameter comprises at least one of the phase and the amplitude of the emitted and reflected wave. More preferred, the emitted and reflected wave are compared with each other with respect to both of these measurement parameters.

According to the invention, these advantages can also be achieved in a method in which the wave is generated inside a resonator defining at least one discrete resonance frequency of the wave. The method comprises the step of setting the frequency of the wave to a resonance frequency of the resonator at the momentary operation conditions and of emitting an energy fraction of the wave from the resonator towards the blade tip. The method further comprises the step of comparing at least one measurement parameter of the wave emitted towards the blade tip with the corresponding measurement parameter of the wave reflected from the blade tip. Thus, the comparison of the measurement parameter can be advantageously related to the operational state of a rotor blade irrespective of the momentary operation conditions within the turbine environment, such as a temperature gradient.

Preferably, the comparison of a measurement parameter of the emitted and reflected wave is used to obtain information with respect to the relative position and/or relative motion of one or more rotor blades. In a first preferred implementation of the method, the radial gap in between the resonator and the blade tip is deduced from this comparison. Accordingly, the measuring unit of the monitoring device is preferably configured with logic to relate the comparison of the measurement parameter to the radial gap in between the resonator and the blade tip. In this way, clearance measurements between the tips of the rotor blades and the stationary case of the turbine may be conducted. Preferably, the phases of the emitted and reflected wave are used as a measurement parameter to determine the radial gap in between the resonator and the blade tip.

In particular, the clearance between the tips of rotor blades and the stationary engine case can be used as a critical parameter with respect to the efficiency of the turbine. Thus, tip clearance measurements may be primarily focused on improving turbine efficiency through leakage reduction that may be achieved by a reduction in clearance. More specifically, for a given operating state of the turbine the tip clearance should be preferably reduced as much as possible whilst avoiding blade rubbing.

Accurate tip clearance measurement may offer three major advantages:
- it may be used to enable closed loop active clearance control on a turbine, which allows reducing the clearance between the blade tips and the case as much as possible. As a consequence the turbine efficiency can be improved, the specific fuel consumption reduced and undesirable emissions such as NOx and $CO_2$ limited to a minimal value;
- it may be used to help to prolong a turbine lifecycle by preventing a blade from rubbing which may result from a case distortion, rotor dynamics/shaft bending or environmental factors, by preventing blade cycling damage and by increasing hot gas path component life through reduced EGT (exhaust gas temperature); and
- it may be used to provide dimensional measurement from each blade, which may allow prognostics and optimised condition-based maintenance in the turbine hot section.

Furthermore, in axial compressors, tip clearance measurements can be used as a key to compressor stability and stall margin.

Turbine locations on which blade tip clearance measurements are preferably applied include a high-pressure turbine and/or a high-pressure compressor, which are expected to bring the most benefits.

In a second preferred implementation of the method, the comparison of a measurement parameter of the emitted and reflected wave is used to determine a time difference during which a subsequent passage of one rotor blade or of two different rotor blades occurs. Accordingly, the measuring unit of the monitoring device is preferably configured with logic to relate the comparison of the measurement parameter to a time difference during which a subsequent passage of one rotor blade, in particular after one or more revolutions, or of two different rotor blades, in particular of two neighbouring or two diametrically opposing rotor blades, occurs. In this way, time of arrival measurements on a rotor blade may be conducted. Preferably, the amplitudes of the emitted and reflected wave are used as a measurement parameter to determine the time difference during which a subsequent passage of one rotor blade or of two different rotor blades occurs.

Such a time-of-arrival (also called tip timing) measurement can be primarily focused on the mechanical integrity of rotating blades by providing a measure of blade vibration. The measurement preferably consists of detecting the time at which a point on a rotating blade tip passes a stationary point (hence the term "time-of-arrival"). In the absence of blade structural vibration, the time-of-arrival normally depends only on the rotational speed of the blade. However, when a blade structural vibration occurs, the time-of-arrival also depends on the amplitude, frequency and phase of vibration.

Accurate time-of-arrival measurement may offer the following advantages:
- by measuring the blade time-of-arrival, any anomalous signal predicting advanced blade or disk failures can be detected and damages can be avoided through prompt reaction. Time-of-arrival can therefore be used as a key measurement for predicting component life and enables thus condition-based maintenance;
- it can be used to enable safety monitoring during early testing of new turbine engine designs and can help to validate these new designs during development engine testing; and
- it can be used to enable the measurement of asynchronous vibrations for blade flutter, rotating stall and compressor surge detection.

Turbine locations on which time of arrival measurements are preferably applied include the early stages of a low-pressure compressor up to the rear stages of a high-pressure compressor, which are expected to bring the most benefits.

In general, land-based turbines, aero-derivatives, aero-ground tests and aero-engines (non-exhaustive list) can greatly benefit from accurate tip clearance and time-of-arrival measurements. Therefore, according to a third preferred implementation of the method, the radial gap in between the resonator and the blade tip and the time difference in between a subsequent passage of rotor blades are deduced from the comparison of the measurement parameter. Accordingly, the measuring unit of the monitoring device is preferably configured with logic to relate the comparison of at least one measurement parameter of the emitted and reflected wave to the radial gap in between the resonator and the blade tip and the time difference in between a subsequent passage of rotor blades. Preferably, at least two measurement parameters, in particular the phases and the amplitudes of the emitted and reflected wave, are used as a measurement parameter to determine both tip clearance and time-of-arrival of the monitored rotor blade independently from each other.

The following preferred aspects of the invention may be advantageously implemented in the monitoring method and/or the monitoring device.

Preferably, the wave emitted through the aperture is characterized by at least two field components: First, a reactive near field can be provided by the emitted wave, in which electromagnetic energy is stored in the absence of a receiving object and which transfers energy in the presence of a receiving object. Preferably, the near field component is measured within a distance from the aperture smaller than the emission wavelength, more preferred within a distance of at most three quarters of the emission wavelength, and most preferred within a distance of at most one half of the emission wavelength. Secondly, a propagating field can be provided by the emitted wave, in particular at significantly larger distances from the aperture as compared to the emission wavelength, which is radiating energy away from the resonator regardless of the presence of a receiving object.

Preferably, the resonator is only resonant for a number of discrete resonance frequencies. Thus, no continuum of resonance frequencies is supported by the resonator. Preferably, the design and geometry of the resonator is chosen to obtain the resonance at a desired operation frequency of the wave, preferably within a frequency range from 1 to 100 GHz. Moreover, the resonator is preferably configured to obtain a resonance for a dominant mode of the wave, such as the TE11-mode or the TEM-mode.

Preferably, the measurement parameter comprises the phase of the emitted and reflected wave. Thus, a phase comparison which is obtained by the measuring unit when the resonator is at resonance may be used to determine the operational state of a respective rotor blade. More preferred, the phase comparison is carried out by determining the phase of the reflection coefficient of the resonator, i.e. the phase component of the ratio between the reflected wave and the transmitted wave. Thus, a measured modification of the reflection coefficient can indicate the presence of a rotor blade and can further be used to determine its operational state. In particular, the quality factor and/or the input match of the emanated and reflected waves may be extracted from the phase comparison.

Alternatively or supplementary, the measurement parameter preferably comprises the amplitude of the outgoing and reflected wave. Thus, a comparison of the amplitudes which is obtained by the measuring unit when the resonator is at resonance may be used to determine the operational state of a respective rotor blade. For instance, the amplitude of the wave may be measured as a power distribution of the wave, in particular a gaussian distribution, wherein the maximum peak and/or integral and/or width of the power distribution may be used to compare the power distributions of the emitted and reflected wave.

According to a first preferred implementation, the comparison of the measurement parameter of the emitted and reflected wave relies at least on the reactive near field of the resonator that is interacting with the rotor blades. In this way, a large transverse resolution of the monitored object can be obtained. According to a second preferred implementation, the comparison of the measurement parameter of the emitted and reflected wave relies at least on the propagating field of the resonator interacting with the rotor blades, providing a large longitudinal range for distance sensing. According to a most preferred implementation, the comparison of the measurement parameter of the emitted and reflected wave relies on the interaction of both field components with the rotor blades in order to combine both advantages.

Preferably, the frequency adjusting unit is configured to vary the wave frequency within at least one predetermined frequency range and to determine the resonance frequency on the basis of the frequency variation. Preferably, the frequency variation is performed to determine and/or adjust at least one of the following parameters according to the momentary operation conditions of the turbine:

the resonance frequency of the resonator, in particular its center frequency;

the phase length on a feeding transmission line connected to the resonator, in particular a coaxial cable connecting the resonator to a wavesource.

In this way, the frequency can be readjusted to allow an accurate blade measurement, e.g. to account for a phase shift of the center frequency of the resonator due to a change of the dielectric constant under temperature. Most preferred, both parameters are determined within one frequency variation. The frequency setting carried out by the frequency adjusting unit may be regarded as a calibration procedure which allows to establish accurate measurement conditions for the blade within a subsequent comparison of the measurement parameter of the measuring unit.

According to a preferred implementation, the change of the resonance frequency of the resonator and/or of the phase length of the feeding transmission line determined during the frequency variation is employed as a reference phase. Preferably, the reference phase is subsequently used by the measuring unit as a measurement parameter of the emitted wave to be compared with the wave reflected from the blade tip.

According to a preferred configuration, the frequency adjusting unit is configured to set the resonance frequency of the resonator each time before and/or after an actual measurement of the operational state of a rotor blade is carried out. For instance, at least one frequency variation can be performed before and/or after a measurement of the measurement parameter. In this way, a highly reliable blade monitoring can be ensured. To further increase the measurement accuracy, repeated frequency variations may be applied before the measurement of the measurement parameter. This may further contribute to a reduction of the measurement noise, e.g. by means of averaging the frequency values that have been determined after each frequency variation.

According to another preferred configuration, the frequency adjusting unit is configured to set the resonance frequency of the resonator each time after a predetermined number of measurements of the rotor blade's operational state or after a predetermined time interval. The latter configurations may be in particular applicable in turbine environments in which only small or exceptional temperature gradients are expected.

Preferably, the resonator is a microwave resonator. Correspondingly, the frequency range in which the resonance frequency of the resonator is set by the frequency adjusting unit lies preferably within the microwave frequency range. The wavesource is preferably constituted by a microwave source.

Preferably, at least one detector that is adapted for a signal detection of the wave in the waveguide and/or emitted from the waveguide and/or reflected from the rotor blade is operatively connected with the frequency adjusting unit and/or the measuring unit. Preferably, the detector comprises at least two detection units, in particular mixers, that are offset in phase in order to allow a phase measurement for the calibration procedure of the frequency adjusting unit and/or for the comparing procedure of at least one measurement parameter of the measuring unit. Preferably, the detector is configured to detect the signal of the wave that is emitted towards the blade tip and the signal of the reflected wave. Suitable algorithms for evaluating the detected signal within the calibration process of the frequency adjusting unit and/or within the comparison of at least one measurement parameter of the measuring unit are known in the art.

The monitoring device according to the invention based on a resonator can provide the advantage of much smaller dimensions as compared to conventional devices. Thus, the applicability of the monitoring device also in smaller spaced turbine environments can be greatly improved. The small dimension of the present device based on a resonator has the further advantage of yielding a smaller spot-size and consequently a larger measurement resolution. Moreover, the exploitation of the resonator's reactive near field rather than the propagating field of a patch antenna allows to further increase the measurement precision.

The frequency adjusting unit and the measuring unit may be realized as a single logical component, program code or the like, or as separate units.

According to a first preferred configuration, the side walls of the resonator are formed by a hollow tube constituting said waveguide. The hollow tube may have a circular, rectangular or other section allowing the guiding of waves. Such a resonator is subsequently referred to as a cavity resonator. It offers the advantage of smaller dimensions and of being less sensitive to the axial position relative to the rotor blade as compared to current measurement devices. Dielectric filling materials can be used to further reduce the size of the cavity resonator. Thus, a particularly preferred application area of the cavity resonator lies in the tip clearance measurement of small turbines, in particular to accommodate a small mounting hole and smaller/thinner blade dimensions.

According to a second preferred configuration, the waveguide is constituted by a central conductor extending coaxially through the resonator. Such a resonator is subsequently referred to as a coaxial resonator. It offers the advantage that a further miniturisation with respect to the cavity resonator is possible, such that the detection spot size can be even further reduced. Furthermore, an excellent waveform with a sharp rise time can be obtained. In particular, the sharper waveform provides the benefit of an improved time resolution. Dielectric filling materials can be used to further reduce the size of the coaxial resonator. Thus, a particularly preferred application area of the coaxial resonator lies in time of arrival measurements requiring a very small spot size and a sharp rise time of the waveform in order to achieve a high spatial resolution.

Preferably, in both configurations of a cavity resonator and a coaxial resonator the monitoring of the rotor blades is based upon a combination of reactive near field and propagating field interaction with the rotor blades. In particular, the contribution of the reactive near field can be advantageously exploited to achieve a high spatial resolution of the measurement as compared the current monitoring devices.

Preferably, the aperture at the front end of the resonator is covered by a protective cap. The protective cap is preferably used to prevent a contamination of the cavity of the resonator. More preferred, the protective cap consists of a dielectric material for high temperature applications. Preferably, the electromagnetic wave is generated in the resonator at the opposite side of the protective cap.

Preferably, the cavity of the resonator is filled with a dielectric material. In this way, the size of the resonator can be further reduced. Preferably, the length of the resonator is chosen in such way that the resonator is resonant for at most three quarter of the wavelength corresponding to the excitation frequency, more preferred for at most half of this wavelength, and most preferred for at most a quarter of this wavelength.

In order to ensure the functionality of the monitoring device in a turbine exhibiting a certain temperature gradient, the resonator is preferably configured to be resonant for at least one frequency of the varied frequency range for all temperatures within an intended operation temperature range. Preferably, the operation temperature range comprises a temperature value of at least 600 K, more preferred at least 900 K, and most preferred at least 1300 K. Preferably, the operation temperature range also comprises low temperature values of below 230 K. In this way, the requirements of specific turbine environments, such as the rear stages of a high-pressure compressor of aero-engines or high-pressure turbines, can be accounted for.

To further enable the monitoring device to operate within the harsh conditions of specific turbine environments, the resonator preferably consists of a material that is resistant to a temperature of at least 900 K, more preferred at least 1300 K. Preferably, the material of the resonator comprises at least one high temperature resistant metal or metal alloy.

In order to generate the wave directly in the waveguide, the wavesource is preferably connected to an excitation probe extending into the cavity of the resonator. The excitation probe can be shaped as a pin, an open loop or a closed loop, wherein also other shapes are conceivable which allow an excitation of the resonator for the desired frequency range. In many applications, loops may be advantageous in that they offer superior excitation properties.

A suitable transmission line for connecting the excitation probe with the wavesource is preferably constituted by the inner conductor of a coaxial cable. More preferred, the excitation probe is constituted by an end portion of the inner conductor that is protruding from the coaxial cable. Preferably, a high temperature coaxial cable is used. More preferred, the coaxial cable is bond to the outer surface of the resonator and the protruding end portion extends via a through hole inside the cavity. The joint in between the coaxial cable and the resonator is preferably realized using a braze, TIG welding, laser welding, or any other metal-to-metal joining technique.

According to a first preferred configuration, the excitation probe is connected with the wavesource through a hole in the back end of the resonator. According to a second preferred configuration, the excitation probe is connected with the wavesource through a hole in a lateral side wall of the resonator, more preferred at an end portion of the side wall that is close to the back end. Both configurations may be advantageous with respect to the mounting of the resonator in a turbine depending on the respective application area.

The present invention also relates to a turbine, in which the above described monitoring device is mounted. Preferably, the monitoring device is mounted in such a way, that measurements based on the reactive near field interaction with the rotor blades can be accomplished. Thus, the resonator is preferably disposed in such a way that the radial gap in between the front end and the passing blade tip is at most three quarters, more preferred at most one half, of the wavelength which corresponds to the wave frequency within the turbine propagation medium for all temperatures within the intended operation temperature range. Preferably, the temperature range comprises a temperature value of at least 600 K, more preferred at least 900 K, and most preferred at least 1300 K. Preferably, the temperature range also comprises low temperature values of below 230 K. Preferably, the monitoring device is mounted in the housing of the turbine.

BRIEF DESCRIPTION OF THE DRAWINGS

The invention will be described in more detail in the following description of preferred exemplary embodiments with reference to the accompanying drawings. In the drawings.

DETAILED DESCRIPTION OF PREFERRED EMBODIMENTS

Figure 1:
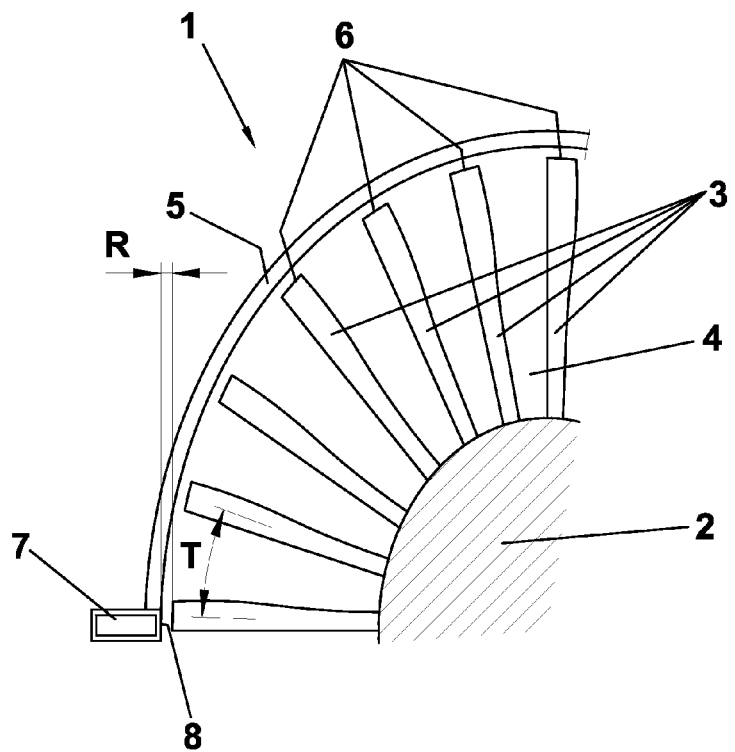
FIG. 1 is a schematic view of a turbine comprising a device for monitoring the operational state of the rotor blades.

The turbine 1 depicted in FIG. 1 comprises a rotor shaft 2 on which rotor blades 3 are fixed in a flow channel 4. The flow channel 4 is circumferentially bordered by a housing 5 surrounding the respective tip 6 of each rotor blade 3. A resonator of a device 7 for monitoring the operational state of the rotor blades 3 is mounted in the housing 5. In order to improve the reliability of the measurement in certain turbine environments, the resonator is preferably set back within the housing 5 in such a way, that its front end 8 has a larger spacing R from the respective tip 6 of a passing rotor blade 3 as compared to the adjoining inner wall of the housing 5. In other turbine environments, the resonator may also have the same spacing R from the tip 6 of a passing rotor blade 3 as compared to the inner wall of housing 5 or extend into the housing.

The device 7 is employed to measure the distance R in between the tip 6 of a passing rotor blade 3 during the operation of turbine 1, i.e. to determine the clearance of a passing tip 6. A deviation from a standard value indicates that the turbine efficiency is suboptimal and that a leakage flow may occur. The device 7 is further employed to measure the time difference T in between a subsequent passage of two rotor blades 3 and/or the time difference T in between a subsequent passage of one particular rotor blade 3 after one or several revolutions. A deviation from a standard value, in particular with respect to the rotational speed of rotor shaft 2, indicates that vibrations on a rotor blade 3 do occur. If the detected vibrations are larger than a predicted value, a damage of this rotor blade 3 must be suspected.

Figure 2:
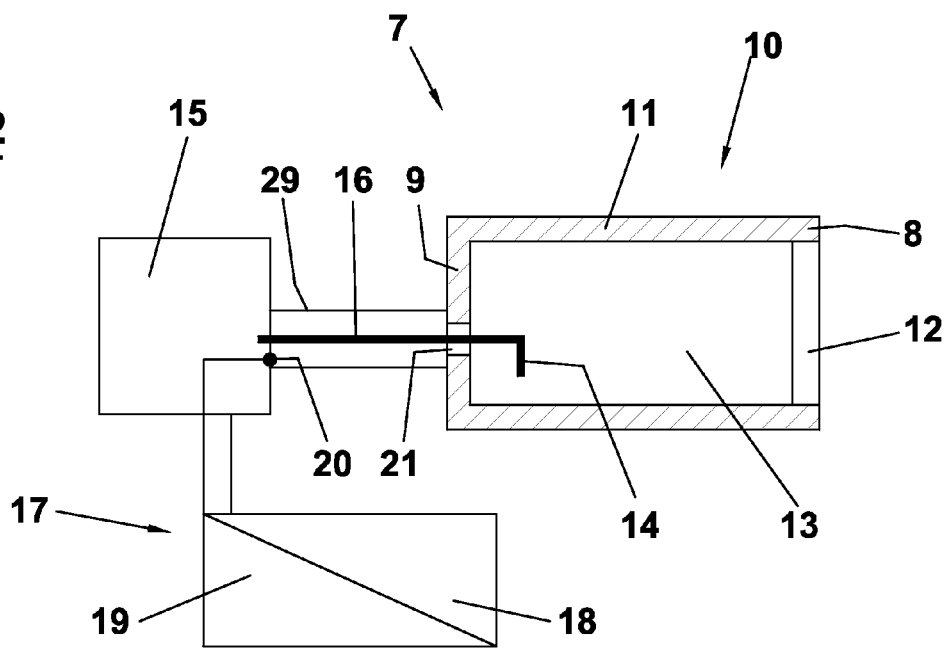
FIG. 2 is a more detailed schematic view of the monitoring device shown in FIG. 1.

FIG. 2 schematically illustrates the assembly and functionality of the monitoring device 7. The device 7 comprises a resonator 10 with an open circuited front end 8 and a short-circuited back end wall 9. The lateral sides of resonator 10 are constituted by a hollow tube 11 forming a waveguide. The length of waveguide 11 is chosen to be optimized for a desired resonance frequency of the resonator 10. The aperture of the open front end 8 is covered by a protective cap 12.

Thus, the resonator 10 is based on a piece of waveguide 11, circular, rectangular or other, that is operating in its fundamental propagating mode (TE11 for a circular waveguide for example). It is terminated on one end 9 by a short circuit and on the other end 8 by an open circuit, being thus resonant for a length that is for instance roughly equal to a quarter wavelength at the operating frequency.

An excitation probe 14 extends from the back end wall 9 of resonator 10 into its cavity 13. A resonator 10 according to this specific embodiment is subsequently referred to as an end-launch cavity resonator. The excitation probe 14 is connected with a wavesource 15 via a feeding transmission line 29 which is constituted by a coaxial cable. The back end wall 9 is provided with a joint 21 comprising a through hole through which the central conductor 16 of the coaxial cable 29 passes. In this way, the cavity 13 can be excited by the excitation probe 14. Thus, an electromagnetic wave can be generated in the waveguide 11 at the resonance frequency of resonator 10. The wavesource 15 is typically working at a microwave frequency and the resonator 10 and excitation probe 14 are optimized for this frequency range.

At resonance, the electromagnetic signal coming from the transmission line 16 is coupled into the cavity 13. The microwave resonator 10 then emits a fraction of the electromagnetic energy at its open end 8 and produces both propagating (radiating) and reactive fields, which are different behaviour characteristics of the electromagnetic field emanating from the source 10. Propagating fields radiate energy away from the source regardless of whether there is a receiving circuit. On the other hand, reactive fields store energy in the absence of a receiving circuit whereas in the presence of a receiving circuit, reactive fields transfer energy. At the open-ended side 8 of the cavity 13, reactive near field and propagating field components thus exist, and interact with any target passing in front of the sensor 10. The reactive near field component provides transverse resolution, and the propagating field component provides longitudinal range for the distance sensing.

Preferably, the resonator 10 is arranged in the housing 5 of turbine 1 in such a way, that the radial gap R in between the front end 8 and the blade tips 6 lies within a preferred measurement range RND for the reactive near field of resonator 10. The distance RND is preferably defined as: RND<$\lambda$/2, wherein $\lambda$ is the emission wavelength of the resonator 10. This advantageously allows to exploit the combined field ranges of the reactive near field and the propagating field for the monitoring of the rotor blades 3. In principle, an operation within the reactive near field range up to one half of the emission wavelength is preferred, in order to avoid ambiguities of measuring multiple wavelengths. However, also an operation in the far field range is conceivable.

Preferably, the monitoring at the position of the blade tips 6 mostly relies on the reactive near field component yielding the advantage of an increased transverse resolution of the measurement. The relation of reactive near field to propagating field at the open-ended side 8 of the resonator 10 depends on the relation of the transverse dimension of the resonator 10 to the wavelength: the smaller the electrical dimension, the higher the proportion of reactive near field is. This fact provides guidance during the design phase based upon application requirements.

The transverse dimension of the cavity resonator 10 is selected in such a way that for the operating frequency (for example 24 GHz), the dominant mode of the corresponding waveguide 11 can be propagated but not the first higher order mode. This means that the section of the cavity resonator 10 can not be smaller than a certain dimension, linked to the cutoff frequency of the dominant mode for the given dimension. Filling the cavity resonator 10 with a dielectric material allows further miniaturisation of its transverse dimension. The longitudinal dimension of the cavity resonator 10 is also given by the operating frequency. It is chosen in such a way to obtain a resonance at the operating frequency, and could for instance correspond to a quarter guide wavelength.

The resonance frequency of the resonator 10 is therefore defined by its length, inner diameter and the dielectric permittivity of the protective cap and, if applicable, of the filling dielectric material of the resonator. The resonance frequency thus depends on the temperature, due to the permittivity variations and dimension variations induced by a change in temperature. The position, dimension and shape of the excitation probe 14 define the coupling of the microwave signal into the resonator 10. These features should be adjusted in order to obtain a critical coupling of the resonator 10 to the central conductor 16 of coaxial cable 29.

The monitoring device 7 further comprises a signal processing unit 17 that is functional to prepare and conduct the signal processing for the monitoring process of the rotor blades 3. For this purpose, the signal processing unit 17 comprises a frequency adjusting unit 18 and a measuring unit 19. Both, the frequency adjusting unit 18 and the measuring unit 19 are operatively connected with at least detector 20 disposed at the end of transmission line 20 that is opposed to resonator 10. Furthermore, the frequency adjusting unit 18 is operatively connected with the wavesource 15.

The frequency adjusting unit 18 is functional to set the excitation frequency of excitation probe 14 to the resonance frequency of resonator 10 according to its momentary operation conditions, which are in particular influenced by its momentary operation temperature, as described above. For this purpose, the frequency adjusting unit 18 is configured to sweep the frequency of wavesource 15 within at least one predetermined frequency band. By varying the frequency of the signal transmitted from wavesource 15, the frequency adjusting unit 18 changes the total amount of phase length between the wavesource 15 and the resonator 10 in order to accurately locate the resonance (i.e. the center frequency of the resonance of the resonator 10) and to measure changes in the phase length of the feeding transmission line 16.

Both parameters can change under temperature due to the change in dielectric constant when the materials in the transmission line 16 or resonator 10 heat up. Therefore, the resonator 10 is prone to change its center frequency with temperature. According to one embodiment of the invention, the phase measurement conducted in the frequency sweep can be employed as a reference phase used by the measuring unit 19 to compare with the phase of the wave reflected from the blade tip 6.

In the case of a negligible temperature change in the environment, this reference phase does not change. If the transmission line 16 and resonator 10 are not changing temperature or not changing very fast, then the frequency sweep can be done on a periodic basis (e.g. minutes to hours). Preferably, frequency sweeps for measurements in a harsh environment are repeated at a much faster rate, for instance in the range of once per second (for tip clearance measurements) or continuously (for time of arrival measurements).

The measuring unit 19 is functional to compare at least one measurement parameter of the wave emitted towards the blade tip with the corresponding measurement parameter of the wave reflected from the blade tip. The measurement parameter comprises the phase and/or the amplitude of the wave in order to perform tip-clearance and/or time-of-arrival measurements. In this way, the difference of the measurement parameters of the microwave signal reflected by the resonator at resonance and out of resonance can be used to determine the distance and/or nature, for example the shape, of the rotor blade 3 passing in front of the resonator 10.

In particular, the phase of the reflection coefficient of the resonator 10 and/or the difference of the amplitude between the outgoing and reflected wave is determined by measuring unit 19. The measurement unit 19 is enabled to perform this measurement in a reliable manner since the resonance frequency has been obtained and adjusted beforehand by the frequency adjusting unit 18. This allows to take into account the changes in dimension and dielectric permittivity due to large thermal gradients present in the harsh environment of turbines, and allows performing accurate measurements even if the resonance frequency of the resonator 10 shifts with temperature. Thus, the modification of the phase of the reflection coefficient of the resonator 10, in particular due to reactive near field interaction and/or propagating field interaction with the target 3, and/or the difference of the amplitude between the outgoing and reflected wave provides a significant monitoring parameter of the operational state of the rotor blades 3.

The comparison of the measurement parameter carried out by measuring unit 19 is based on the signal detected by detector 20. For the purpose of a phase detection, detector 20 comprises at least two detection units, in particular mixers, that are offset in phase. The phase offset preferably corresponds to 90 degrees. In this way, an in-phase signal and a quadrature signal can be obtained. The phase component of the vector corresponding to these two signals can be derived according to algorithms known in the art. Note that a varying DC component, causing an unwanted shift of this vector by a constant value, can be effectively avoided by the frequency adjustment performed by the frequency adjustment unit 18. Accordingly, the detector 20 further allows to determine the amplitude of the wave.

Figure 3:
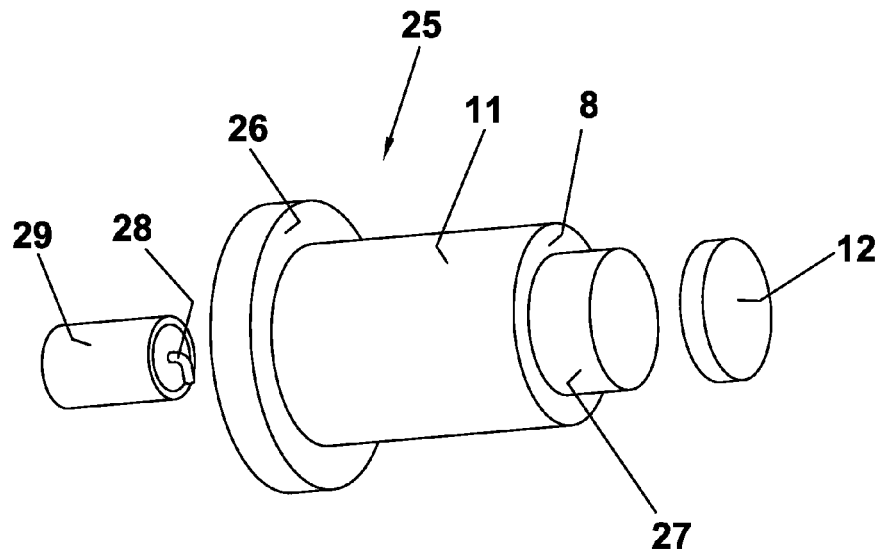
FIG. 3 is an exploded view of an end launch cavity resonator that can be applied in the monitoring device shown in FIG. 2.
Figure 4:
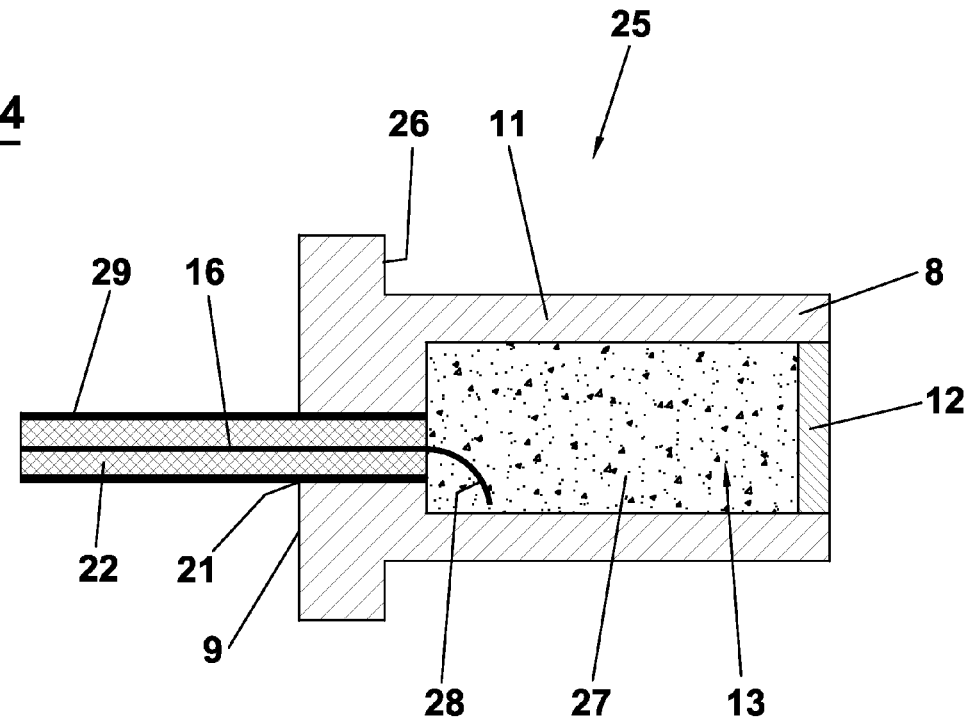
FIG. 4 is a sectional view of the resonator shown in FIG. 3.

FIGS. 3 and 4 show a resonator 25 according to a first alternative embodiment that can be used in the place of resonator 10 in the device shown in FIG. 2. This resonator is also referred to as an end-launch cavity resonator 25. Identical constituent parts with respect to the previously described resonator 10 are labelled with the same reference numerals. Further depicted in FIGS. 3 and 4 is the coaxial cable 29, in which the feeding transmission line 16 is implemented, surrounded by a dielectrics 22. An excitation probe 28 is constituted by an end portion of this transmission line 16 projecting from the coaxial cable 29 and its dielectric filling 22 into the cavity 13. The excitation probe 28 exhibits a curved shape.

The cavity 13 of resonator 25 is filled by a dielectric material 27 which allows to reduce its transverse dimension by maintaining a desired value or desired value range of its resonance frequency. The back end of resonator 25 is provided with an annular flange 26 which allows a simplified mounting of the resonator 25 in the housing 5 of turbine 1.

Thus, the cavity resonator sensor according to this embodiment is composed of a circular waveguide-based cavity resonator body 25, a feeding coaxial cable 29, with its inner conductor 16 acting as the excitation probe 28, a cavity filling dielectric material 27 and a protective cap 12. The feeding coaxial cable 29, including the dielectric material 22 and inner conductor 16, has the capability to transmit a microwave signal at very high temperature. The length of the resonator body 25 is equivalent to a portion of the guided wavelength at the operating frequency. The section of the resonator body 25 is circular, but it could also be rectangular or exhibit any other adequate shape. It is designed in such a way that the dominant mode of the waveguide 11 propagates at the operating frequency but not the first higher order mode. Preferably, dielectrics 27 other than air are used to further reduce the size of the cavity.

The cavity resonator body 25 is made out of a high-temperature material. Preferably, the resonator comprises a high temperature resistant metal or metal alloy. Alternatively, any material that withstands the installation and environmental requirements could be used. The protective cap 12 is made of a dielectric material for high-temperature applications and is mounted at the front of the cavity 13 of resonator body 25.

Moreover, the protective cap 12 is hermetically sealed to the cavity resonator body 25 by using vacuum brazing or diffusion bounding. The feeding coaxial cable 29 and the protective cap 12 are hermetically sealed to the cavity resonator body 25 to prevent contamination and oxidation of the feeding coaxial cable 29. High-temperature joining techniques, such as brazing or diffusion bonding, are used to join components of the cavity resonator sensor 25. Joint 21 is typically a laser weld or a TIG weld. Other suitable materials and/or welding techniques are known in the art.

Thus, the cavity 13 is based on a circular waveguide 11 short-circuited at one end 9 and open-circuited at the other end 8. The cavity filling dielectric material 27 is used to further reduce the size of the cavity. The inner conductor 16 of the microwave cable 29 forms an open loop and acts as the excitation probe. It excites the appropriate mode in the cavity, in this case a TE11n mode. As it is required that only the dominant mode can propagate in the waveguide 11, all the possible cavity modes of this resonator 25 are of the TE11n type.

Figure 5:
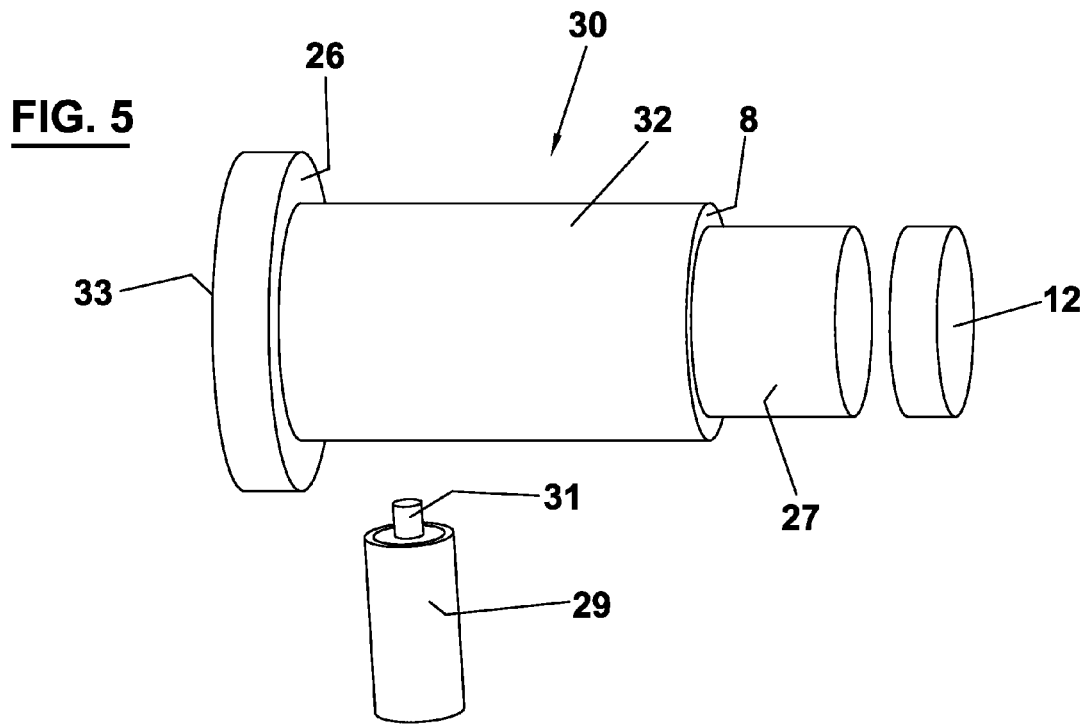
FIG. 5 is an exploded view of a side launch cavity resonator that can be applied in the monitoring device shown in FIG. 2.
Figure 6:
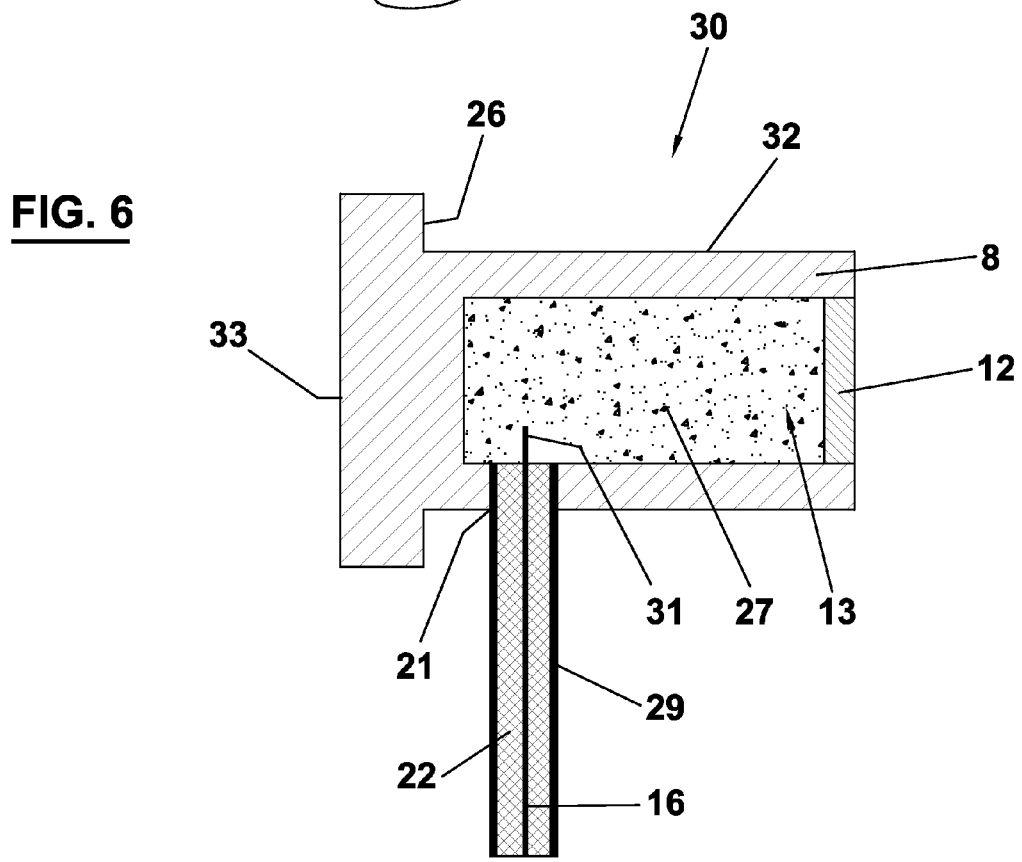
FIG. 6 is a sectional view of the resonator shown in FIG. 5.

FIGS. 5 and 6 show a resonator 30 according to a second alternative embodiment which can be used in the place of resonator 10 in the device shown in FIG. 2. This embodiment is referred to as side-launch cavity resonator 30. Thereby, identical constituent parts with respect to the previously described embodiments 10, 25 are labelled with the same reference numerals. The side-launch cavity resonator 30 essentially corresponds to the end-launch cavity resonator 25 shown in FIGS. 3 and 4, with the exception, that its excitation probe 31 extends into cavity 13 from the side walls 32. Thus, joint 21 is located at an end portion of side walls 32. Apart from this difference, the side walls 32 substantially correspond to the waveguide 11 of resonator 25. Correspondingly, the back end 33 of resonator 30 substantially corresponds to the short-circuited back end 9 of resonator 25, with the exception, that no joint for a coaxial cable is provided.

Thus, the side-launch cavity resonator sensor is composed by a circular waveguide-based cavity resonator body 30, a feeding coaxial cable 29, with its inner conductor 16 acting as the excitation probe, a cavity filling dielectric material 27 and a protective cap 12. The feeding coaxial cable 29, including dielectric material 22 and inner conductor 16, has the capability to transmit microwave signal at very high temperature. The main difference with the end-launch cavity resonator sensor 10, 25 is that the fundamental mode in the cavity is excited on its side 32 rather than at its end 33.

The cavity filling dielectric material 27 is used to further reduce the size of the cavity 13. The protective cap 12 is hermetically sealed to the cavity resonator body 32 by using vacuum brazing or diffusion bounding. The high-temperature microwave cable 29 is hermetically sealed to the cavity resonator body 30. The inner conductor 16 of the microwave cable 29 forms a pin 31 projecting into cavity 13 which acts as the excitation probe. The feeding coaxial cable 29, including its dielectric material 22 and inner conductor 16, has the capability to transmit a microwave signal at very high temperature.

Figure 7:
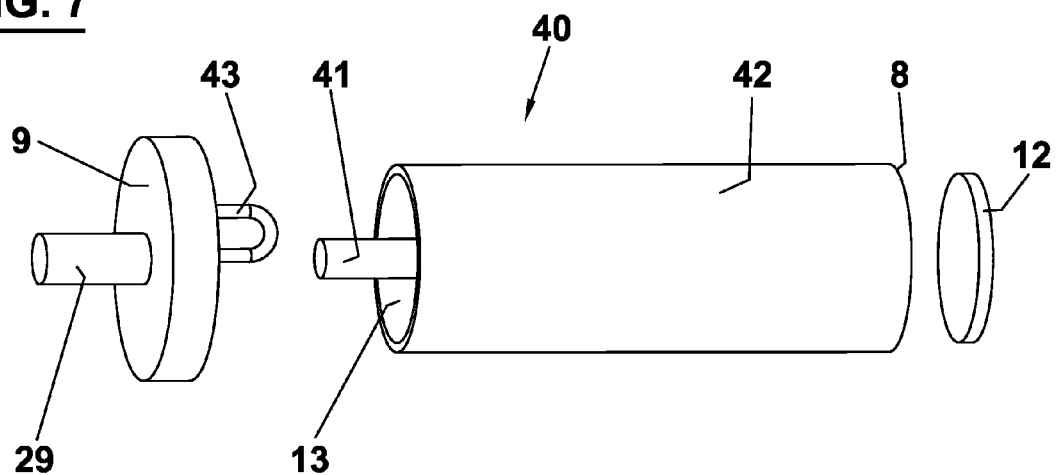
FIG. 7 is an exploded view of a coaxial resonator that can be applied in the monitoring device shown in FIG. 2.
Figure 8A:
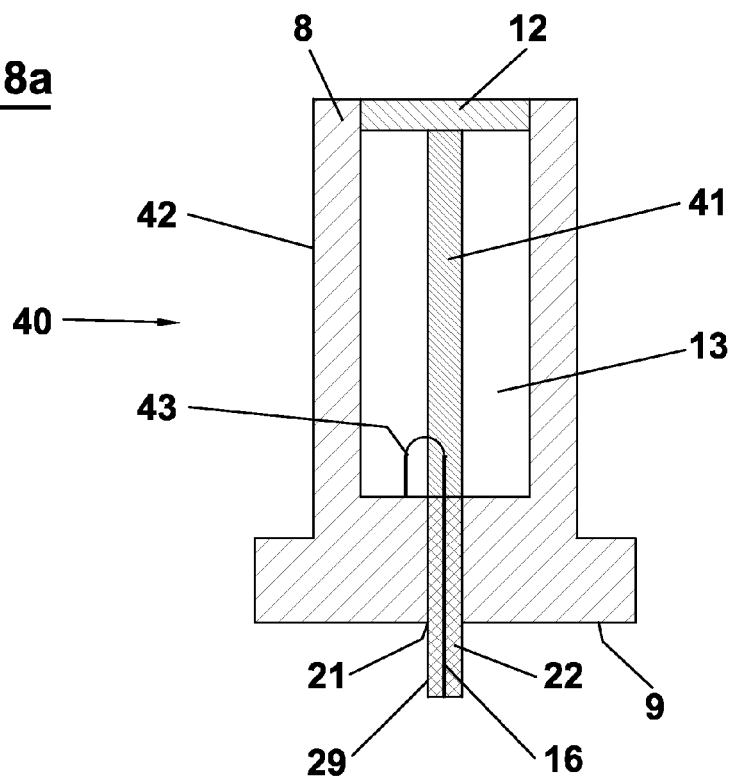
FIG. 8a, b are sectional views of the resonator shown in FIG. 7.
Figure 8B:
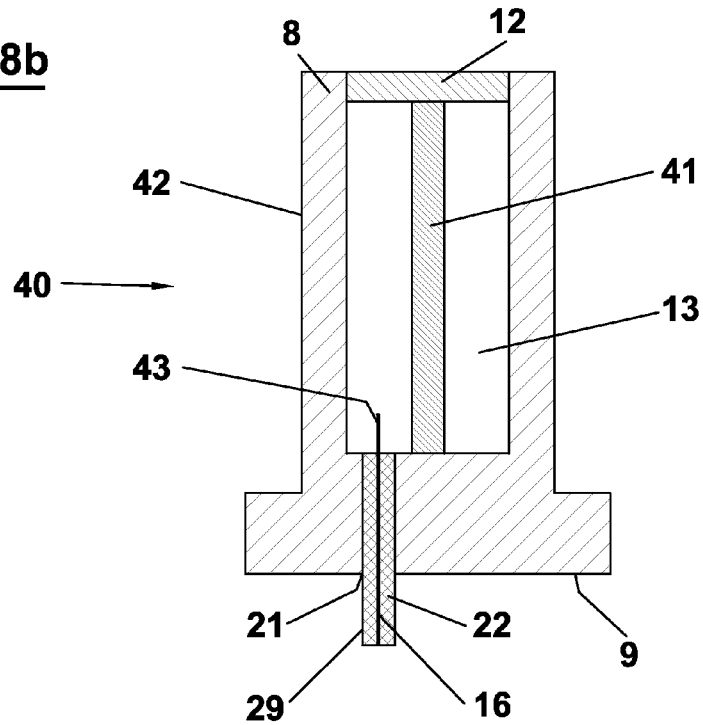
Figure 9A:
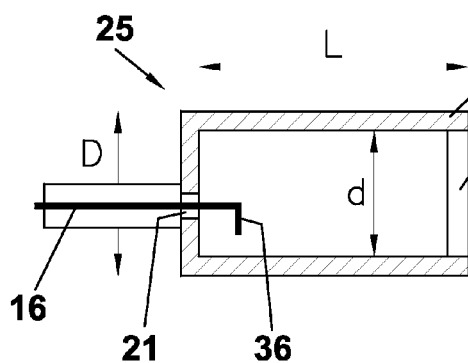
FIG. 9a-d are schematic illustrations of the resonators shown in FIG. 3 to 8 with various embodiments of the excitation probes.
Figure 9B:
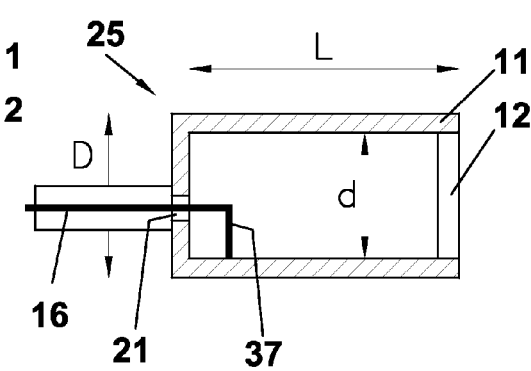
Figure 9C:
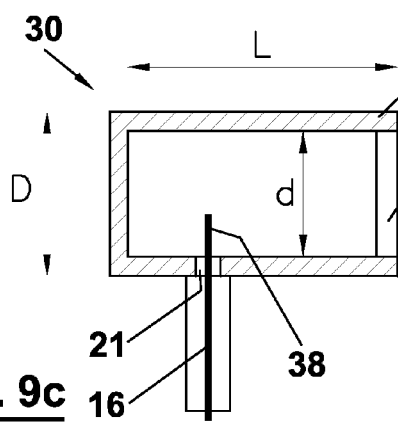
Figure 9D:
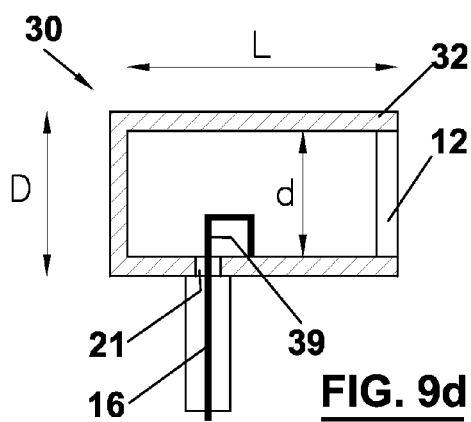
Figure 10A:
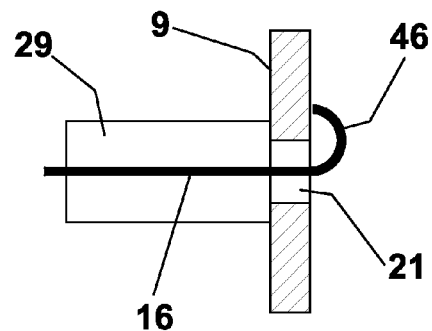
FIG. 10a-f are schematic illustrations of the back end of the resonators shown in FIG. 3 to 8 with various embodiments of the excitation probes.
Figure 10B:
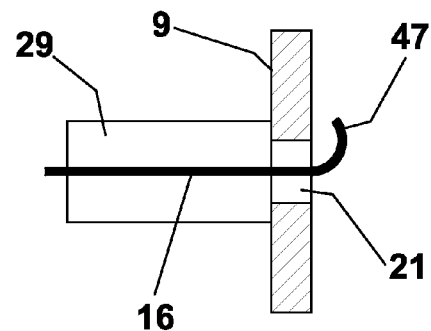
Figure 10C:
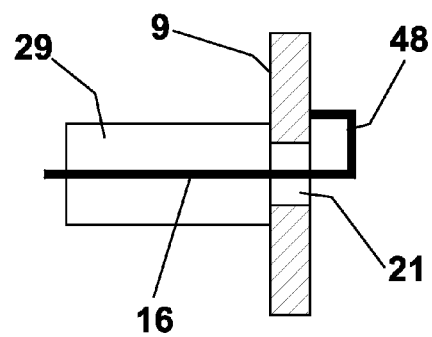
Figure 10D:
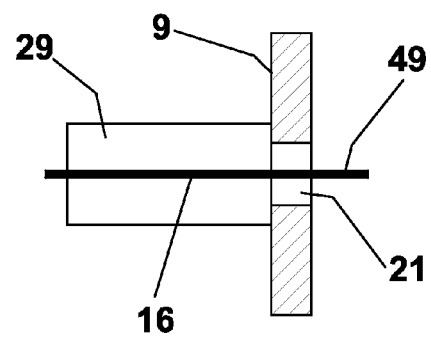
Figure 10E:
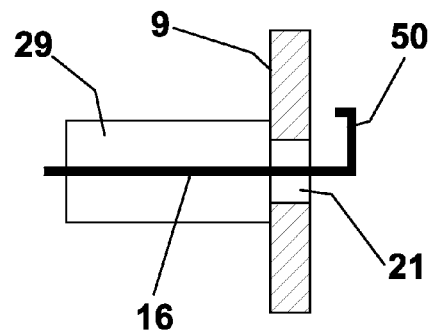
Figure 10F:
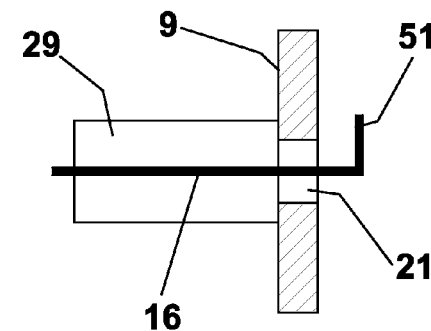

FIGS. 7 and 8a, b show a resonator 40 according to a third alternative embodiment that can be used in the place of resonator 10 in the device shown in FIG. 2. The resonator according to this embodiment is referred to as coaxial resonator 40. Identical constituent parts with respect to the previously described embodiments 10, 25, 30 are labelled with the same reference numerals. The resonator 40 essentially corresponds to the resonator 25 shown in FIGS. 3 and 4, with the following exceptions: first, a central conductor 41 is arranged inside the cavity 13 extending coaxially through its total length and constituting the waveguide of resonator 40. Secondly, the general shape of the side walls 42 of resonator 40 correspond to the hollow tube 11 of resonator 25, but their transverse dimension can be advantageously reduced. Furthermore, excitation probe 43 is shaped differently.

In detail, the coaxial resonator 40 comprises an outer conductor 42 and an inner conductor 41, having the same axis. The coaxial resonator 40 is terminated by a short circuit at its back end 9 and an open circuit at its front end 8. The coaxial resonator 40 is further provided with the feeding coaxial cable 29, which feeds the excitation probe 43. The excitation probe 43 in this example is a closed loop and excites the coaxial resonator 40. The dimension, shape and position of the excitation probe 43 are optimised in order to obtain a good impedance matching at the desired operating frequency. The front end of the coaxial resonator 40 is protected by a protective cap 12. The coaxial resonator 40 can be filled with air or any other adequate dielectrics.

The length of the coaxial resonator 40 is chosen in order to obtain a longitudinal resonance of the coaxial resonator 40. The transverse dimensions of the coaxial resonator 40 are chosen in such a way that only the dominant TEM mode propagates into the corresponding transmission line.

For low-temperature applications, i.e. up to typically 500 K, the protective cap 12 can be glued hermetically to the outer conductor 42. For medium-temperature applications up to typically 900 K, the thermal expansion of different materials and thermal gradient should be considered for the design. High-temperature joining techniques, such as brazing or diffusion bonding, are typically used to join the protective cap 12 to the outer conductor 42. The reliability of the sensor 40 is further increased by choosing an optimum alloy or metal with a low coefficient of thermal expansion. The high-temperature join 21 shown in FIG. 8a, b can be recessed to further improve its life cycle.

Thus, the coaxial resonator 40 is based on the same principle as the cavity resonator 10, 25, 35. The main difference between the coaxial resonator 40 and the cavity resonator 10, 25, 35 is that the waveguide is based on a section of rigid coaxial transmission line 41 instead of a hollow waveguide 11, 32. The main advantage of this is that further miniaturisation is made possible by the fact that the dominant mode of a coaxial transmission line 41 is the TEM (Transverse Electro Magnetic) mode, which has a zero cutoff frequency. This means that there is no theoretical minimum size for the section of the coaxial resonator 40, the minimum section size being thus dictated by manufacturing issues only. The section, however, has to be selected in such a way that the first higher order mode is below cutoff for the operating frequency. The length of the coaxial resonator 40 is selected in a way that the latter is resonant at the operating frequency. This can for instance correspond to a length of a quarter of the guided wavelength, but other solutions are also possible.

FIG. 9a-d schematically depict cross-sectional views of the cavity resonator 25, 30 based on a circular waveguide, wherein various different embodiments of excitation probes 36-39 are illustrated. L is the length of the resonator 25, 30, 40, equivalent for example to a quarter of the guided wavelength at the operating frequency. D is the outer diameter and d the inner diameter. The parameters L, D, d are chosen in such a way that the dominant mode of the waveguide propagates at the operating frequency but not the first higher order mode. Furthermore, the feeding transmission line 16 (in this case a coaxial cable) and the protective cap 12 are shown. The excitation probe can be for example a coupling pin 38 or a coupling loop 36, 37, 39 in the case of the end launch resonator 25 and the side launch resonator 30. More precisely, the coupling loop can be an open loop 36 or a closed loop 37, 39. Note that these excitation probes 36-39 and their respective arrangement at the back end or side wall are also applicable in the coaxial resonator 40.

FIG. 10*a*-*f* schematically illustrate further embodiments of excitation probes 46-41 on a cavity back wall 9, which are also applicable on a cavity side wall. In the place of the coupling pin 49 also open loops 47, 50, 51 or closed loops 46, 48 are conceivable. Furthermore, circular loops 46, 47 or rectangular loops 48, 50, 51 can be applied.

The position, dimension and shape of the excitation probes 36-39, 46-51 define the coupling of the microwave signal into the resonator. These features should be adjusted in order to obtain a critical coupling of the resonator to the feeding transmission line. In many cases, the coupling loops 36, 37, 39, 46-48, 50-51, in particular the closed loops 37, 39, 46, 48, may offer the advantage of superior excitation properties.

The above described preferred embodiments are intended to illustrate the principles of the invention, but not to limit the scope of the invention. Various other embodiments and modifications to those preferred embodiments may be made by those skilled in the art without departing from the scope of the present invention.

The invention claimed is:

1. A device for monitoring an operational state of rotor blades of a turbine from a position facing a blade tip of a passing rotor blade, the device comprising a wavesource for generating an electromagnetic wave and a waveguide for directing the wave towards the blade tip, wherein said waveguide is included in a resonator defining at least one discrete resonance frequency of the wave on said waveguide and the resonator comprising an aperture at its front end through which an energy fraction of the wave can be emitted towards the blade tip, and the device further comprises a frequency adjusting unit that is configured to set the frequency of the wave to a resonance frequency of said resonator at the momentary operation conditions, and a measuring unit that is configured to compare at least one measurement parameter of the wave emitted towards the blade tip with a corresponding measurement parameter of the wave reflected from the blade tip.

2. The device according to claim 1, wherein said frequency adjusting unit is configured to vary the wave frequency within at least one predetermined frequency range and to determine said resonance frequency on the basis of said frequency variation.

3. The device according to claim 2, wherein said resonator is configured to be resonant for at least one frequency of said frequency range for all temperatures within an intended operation temperature range.

4. The device according to claim 3, wherein said operation temperature range comprises a temperature value of at least 600 K.

5. The device according to claim 1, wherein said resonator consists of a material that is resistant to a temperature of at least 900 K.

6. The device according to claim 1, wherein said measuring unit is configured with logic to relate said comparison of a measurement parameter to a radial gap in between said resonator and the blade tip.

7. The device according to claim 1, wherein said measuring unit is configured with logic to relate said comparison of a measurement parameter to a time difference during which a subsequent passage of one rotor blade or of two different rotor blades occurs.

8. The device according to claim 1, wherein side walls of said resonator are formed by a hollow tube constituting said waveguide.

9. The device according to claim 1, wherein said waveguide is constituted by a central conductor extending coaxially through said resonator.

10. The device according to claim 1, wherein said measurement parameter comprises a phase of the wave.

11. The device according to claim 1, wherein said measurement parameter comprises an amplitude of the wave.

12. The device according to claim 1, wherein said aperture is covered by a protective cap.

13. The device according to claim 1, wherein said wavesource is connected with an excitation probe extending into a cavity of said resonator.

14. The device according to claim 1, wherein a cavity of said resonator is filled with a dielectric material.

15. A turbine comprising the monitoring device according to claim 1.

16. The turbine according to claim 15, wherein said resonator is disposed in such a way that a radial gap in between said front end and the passing blade tip is at most three quarters of the wavelength which corresponds to said wave frequency for all temperatures within an intended operation temperature range.

17. A method for monitoring an operational state of rotor blades of a turbine from a position facing a blade tip of a passing rotor blade, in which an electromagnetic wave is generated by a wavesource and directed towards the blade tip, wherein the wave is generated in a resonator defining at least one discrete resonance frequency of the wave, the frequency of the wave being set to a resonance frequency of said resonator at the momentary operation conditions, wherein an energy fraction of the wave is emitted from the resonator towards the blade tip, and wherein at least one measurement parameter of the wave directed towards the blade tip is compared with a corresponding measurement parameter of the wave reflected from the blade tip.

18. The turbine according to claim 15, wherein said resonator is disposed in such a way that a radial gap in between said front end and the passing blade tip is at most one half of the wavelength which corresponds to said wave frequency for all temperatures within an intended operation temperature range.

19. The device according to claim 1, wherein said resonator consists of a material that is resistant to a temperature of at least 1300 K.

20. The device according to claim 3, wherein said operation temperature range comprises a temperature value of at least 900 K.

21. The device according to claim 3, wherein said operation temperature range comprises a temperature value of at least 1300 K.

* * * * *